US00PP11303P

United States Patent [19]

Saville

[11] Patent Number: Plant 11,303

[45] Date of Patent: Mar. 21, 2000

[54] MINIATURE ROSE PLANT NAMED 'SAVANIGHT'

[75] Inventor: F. Harmon Saville, deceased, late of Newburyport, Mass., by Charles K. Brown, executor

[73] Assignee: Nor'East Miniature Roses, Inc., Rowley, Mass.

[21] Appl. No.: 08/995,574

[22] Filed: Dec. 22, 1997

[51] Int. Cl.[7] ..... A01H 5/00

[52] U.S. Cl. ..... Plt./128

[58] Field of Search ..... Plt./121, 122, 123, Plt./128, 129, 116

[56] References Cited

U.S. PATENT DOCUMENTS

P.P. 6,517 1/1989 Benardella ..... Plt./116

*Primary Examiner*—Howard J. Locker
*Attorney, Agent, or Firm*—Christie, Parker & Hale, LLP

[57] ABSTRACT

A new miniature rose plant variety with many petalled, fragrant pink flowers.

1 Drawing Sheet

BACKGROUND OF THE INVENTION

The present invention relates to a new and distinct variety of rose plant of the miniature rose class, which was created by crossing as seed parent the hybrid tea variety known as 'Taxi' and as pollen parent the variety known as 'Benalav' (U.S. Plant Pat. No. 6,517). The varietal denomination of this new rose is 'Savanight'.

SUMMARY OF THE INVENTION

Among the novel characteristics possessed by this new variety which distinguishes it from its parents and all other varieties of which I am aware is its large, many petalled attractive fragrant pink flowers.

Asexual reproduction by propagation of vegetative cuttings of the new variety as performed in Essex County, Mass. shows that the foregoing and other distinguishing characteristics come true to form and are established and transmitted through succeeding propagations.

COMPARISON WITH PARENTS

Among other respects, the new variety differs from its parents in flower color. 'Taxi' produces red flowers and 'Benalav' flowers are mauve.

BRIEF DESCRIPTION OF ILLUSTRATION

The accompanying illustration shows typical specimens of the flowers of the new variety depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (RHSCC). The terminology used in color description herein refers to plate numbers in the aforementioned color chart. Phenotypic expression may vary with light availability, environmental and cultural conditions.

Parentage:

*Seed parent.*—'Taxi'.

*Pollen parent.*—'Benalav'.

Class: Miniature.

The following observations are made of specimens grown under plastic in Essex County, Mass. during October.

FLOWER

Blooming habit: Recurrent.

A. Bud:

(1) *Size.*—Medium.

(2) *Form.*—Obtuse with acute tip.

(3) *Color.*—When sepals first divide, bud color is between 49C and 49B.

(4) *Sepals.*—Slightly bearded; only slightly longer than bud; near 144A; sepals roll back quickly when a bud starts to open and usually remain at about 45° angle from the peduncle until bloom is fully open then roll back to, and occasionally crossing over the peduncle as blooms age; remain attached.

(5) *Peduncle.*—Length—about 1¼ to 1½ inches. Aspect—straight. Strength—bends with weight of open bloom. Color—near 146B.

B. Bloom:

(1) *Size.*—Average size when fully expanded up to about 2⅛ inches.

(2) *Borne.*—Mostly singly; sometimes in clusters of 2 to 5 to a stem.

(3) *Form.*—Opens flat; petals loosely roll outward.

(4) *Petalage.*—Number of petals under normal conditions about 52 to 62.

(5) *Color.*—Inner petals at center of flower near 55B, reverse near 55C; outer petals near 55C, reverse near 55C; when half-blown inner petals near 55C, reverse near 55C; outer petals near 55C, reverse near 49C; base of petals near 154D; general tonality from a distance medium pink.

(6) *Color change.*—As bloom ages, color changes from near 49C to near 55C to 55B and 55C; then to near 55C and 55D; after three or more days general tonality is medium pink.

C. Petals:

(1) *Texture.*—Medium.

(2) *Appearance.*—Outside satiny, inside satiny.

(3) *Form.*—Outer petals nearly round, graduating to oval inner petals with acute apex.

(4) *Arrangement.*—Irregularly arranged; overlapping, sometimes almost doubling up.

(5) *Petaloids in center.*—About 40 often with streak of white or near 154D.
(6) *Persistence.*—Drop off cleanly in 5 to 8 days.
(7) *Fragrance.*—Very strong.
(8) *Lasting quality.*—About 5 to 8 days on the plant; about 4 to 7 days as a cut flower.

REPRODUCTIVE ORGANS

A. Stamens, filaments and anthers:
*Arrangement.*—Unevenly arranged around styles.
B. Stamens:
*Quantity.*—About 3 to 14.
C. Filaments:
*Approximate length.*—Uneven length and very short.
*General color.*—Near 150D.
D. Anthers:
*Color.*—Near 11D.
E. Pollen
*Color.*—Near 22B.
*Quantity.*—Very little.
F. Pistils:
*Quantity.*—Average number.
G. Styles: Uneven length.
*Color.*—A very pale shade of near 140D.
H. Stigmas:
*Color.*—Near 4D.
I. Hips: None observed, could not get pollen accepted.

Plant

A. Form: Upright.
B. Growth: Vigorous.
*Height.*—About 2 feet high.
*Length of flowering stem.*—Varying in length up to about 9 inches when borne singly.
C. Foliage: Compound of 3 to 5 leaflets, occasionally 7.
*Size.*—Medium to large.
*Quantity.*—Abundant.
*Color.*—New foliage: Upper side near 137C; under side near 139C flushed with near 184C Old foliage: Upper side near 137A; under side near between 191A and 138A.
*Shape.*—Oval, pointed.
*Texture.*—Upper side semi glossy; underside matte.
*Thorns or prickles.*—A few prickles on underside of main leaf stem.
*Edge.*—Serrated.
*Serration.*—Fine, uneven on left side of leaflet, even on right side.
*Leaf stem.*—Near 137C, underside near 144A.
*Stipules.*—Very finely bearded; edges curling back as leaf ages; about 1/7 the length of entire compound leaf.
*Resistance to diseases.*—Blackspot — average. Mildew — average. Rust — average.
D. Wood:
*New wood.*—Near 146A, smooth.
*Old wood.*—Near 137C, smooth.
E. Thorns:
*Quantity.*—Few on main stalk and laterals.
*Form.*—Trim, straight, angled slightly downward.
*Length.*—Up to about 5/16 inch.
*Color.*—Near 31D when young.
*Position.*—Irregular.
F. Prickles:
*Main stalk.*—None.
*Laterals.*—None.
*Leaves.*—A few on underside of leaf stems.
G. Winter hardiness: Needs protection in severe climates.

It is claimed:

1. A new and distinct miniature rose plant of the variety substantially as shown and described.

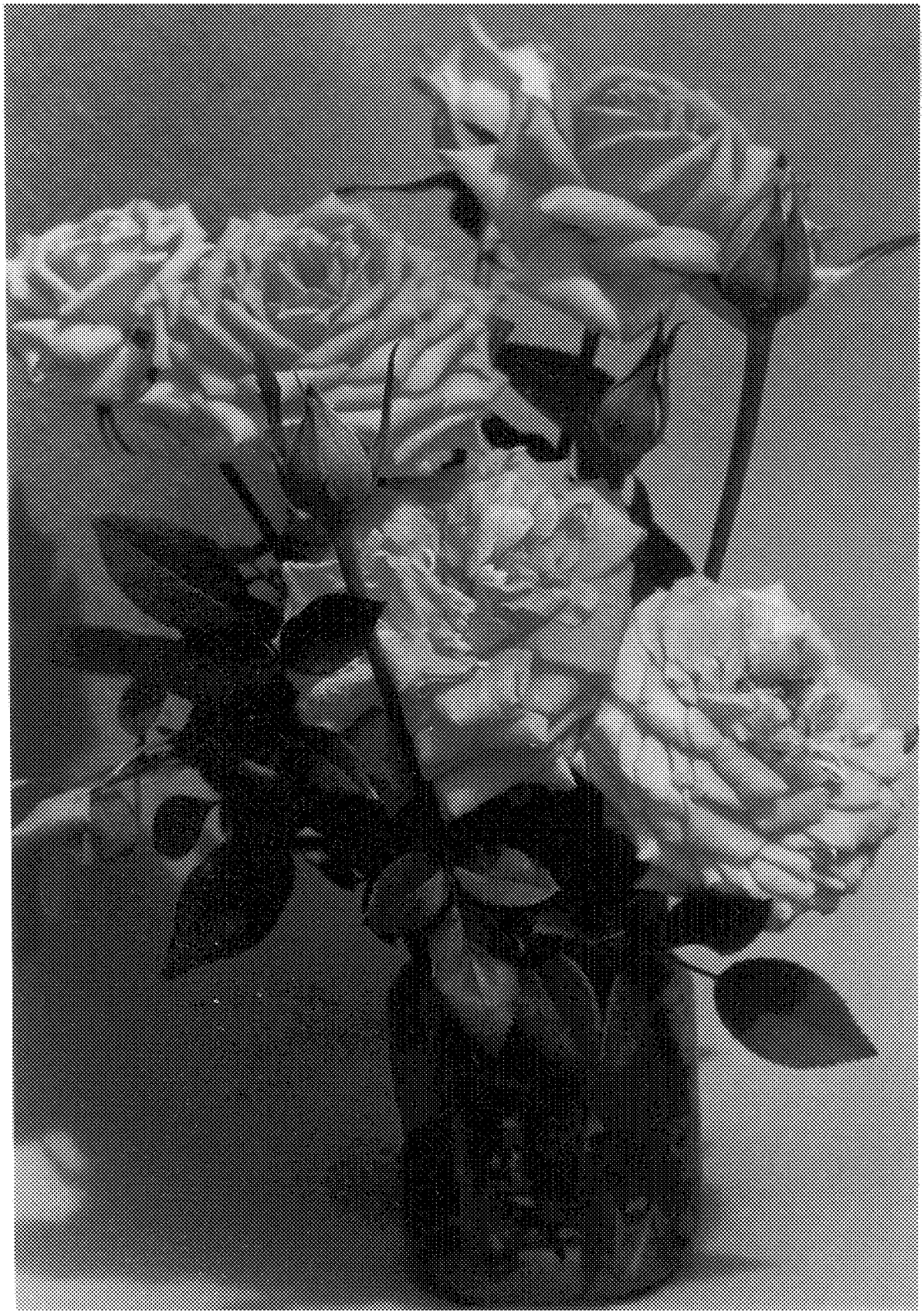

* * * * *